United States Patent
Yamana et al.

(10) Patent No.: US 10,912,452 B2
(45) Date of Patent: Feb. 9, 2021

(54) ILLUMINATION LIGHT GUIDING DEVICE AND ENDOSCOPE DEVICE

(71) Applicant: PANASONIC INTELLECTUAL PROPERTY MANAGEMENT CO., LTD., Osaka (JP)

(72) Inventors: Masahito Yamana, Hyogo (JP); Noboru Iizawa, Osaka (JP); Shintaro Hayashi, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 448 days.

(21) Appl. No.: 15/951,511

(22) Filed: Apr. 12, 2018

(65) Prior Publication Data
US 2018/0303326 A1  Oct. 25, 2018

(30) Foreign Application Priority Data
Apr. 25, 2017  (JP) .................. 2017-086289

(51) Int. Cl.
*A61B 1/06* (2006.01)
*G02B 27/09* (2006.01)
(Continued)

(52) U.S. Cl.
CPC .......... *A61B 1/0653* (2013.01); *A61B 1/0669* (2013.01); *A61B 1/0676* (2013.01);
(Continued)

(58) Field of Classification Search
CPC ... A61B 1/0607; A61B 1/0653; A61B 1/0676; A61B 1/07; G02B 27/0905;
(Continued)

(56) References Cited

U.S. PATENT DOCUMENTS 5,603,687 A * 2/1997 Hori .................. A61B 1/00096
348/45
2003/0042493 A1* 3/2003 Kazakevich ......... A61B 1/0607
257/98
(Continued)

FOREIGN PATENT DOCUMENTS

JP       60-069616      4/1985
JP     2000-121836      4/2000
(Continued)

OTHER PUBLICATIONS

Office Action dated Mar. 20, 2019 issued for the corresponding DE patent application No. 10 2018 109 095.1 and its English machine translation.

*Primary Examiner* — Aaron B Fairchild
(74) *Attorney, Agent, or Firm* — Renner, Otto, Boisselle & Sklar, LLP

(57) ABSTRACT

An illumination light guiding device includes a phosphor layer that is disposed on another surface opposite to one surface of a board, and converts the wavelengths of a plurality of light beams transmitted through the board and incident on one surface of the phosphor layer, and an emission-side fiber including a plurality of optical fibers that are provided so as to be erected side by side on another surface opposite to one surface of the phosphor layer, each optical fiber guiding a different one of the plurality of light beams having wavelengths converted by the phosphor layer.

5 Claims, 8 Drawing Sheets

(51) Int. Cl.
*A61B 1/07* (2006.01)
*G02B 6/04* (2006.01)
*G02B 23/24* (2006.01)
*G02B 27/30* (2006.01)
*F21Y 115/30* (2016.01)
*G02B 6/26* (2006.01)

(52) U.S. Cl.
CPC .............. *A61B 1/07* (2013.01); *G02B 6/04* (2013.01); *G02B 23/2469* (2013.01); *G02B 27/0905* (2013.01); *G02B 27/30* (2013.01); *F21Y 2115/30* (2016.08); *G02B 6/262* (2013.01); *G02B 27/0955* (2013.01)

(58) Field of Classification Search
CPC .. G02B 27/0955; G02B 6/04; G02B 23/2469; G02B 6/0005; G02B 6/0006; G02B 6/0008; G02B 27/30; G02B 27/283; G02B 27/285; F21V 2200/00; F21V 2200/10; F21V 2200/13; F21V 2200/17; F21V 9/30; F21V 9/32
USPC ........................................................ 362/84
See application file for complete search history.

(56) References Cited

U.S. PATENT DOCUMENTS

| | | | | |
|---|---|---|---|---|
| 2013/0345517 A1* | 12/2013 | Morimoto | .............. | H05B 47/10 600/178 |
| 2014/0005483 A1* | 1/2014 | Ohashi | ................ | A61B 1/0646 600/162 |
| 2017/0102139 A1* | 4/2017 | Iizawa | .................... | F21V 29/70 |
| 2018/0066810 A1* | 3/2018 | Lentine | .............. | G02B 19/0061 |
| 2018/0294390 A1 | 10/2018 | Yamana | | |

FOREIGN PATENT DOCUMENTS

| | | |
|---|---|---|
| JP | 2009-189473 | 8/2009 |
| JP | 2016-137308 | 4/2016 |
| WO | 2017/061120 A1 | 4/2017 |

\* cited by examiner

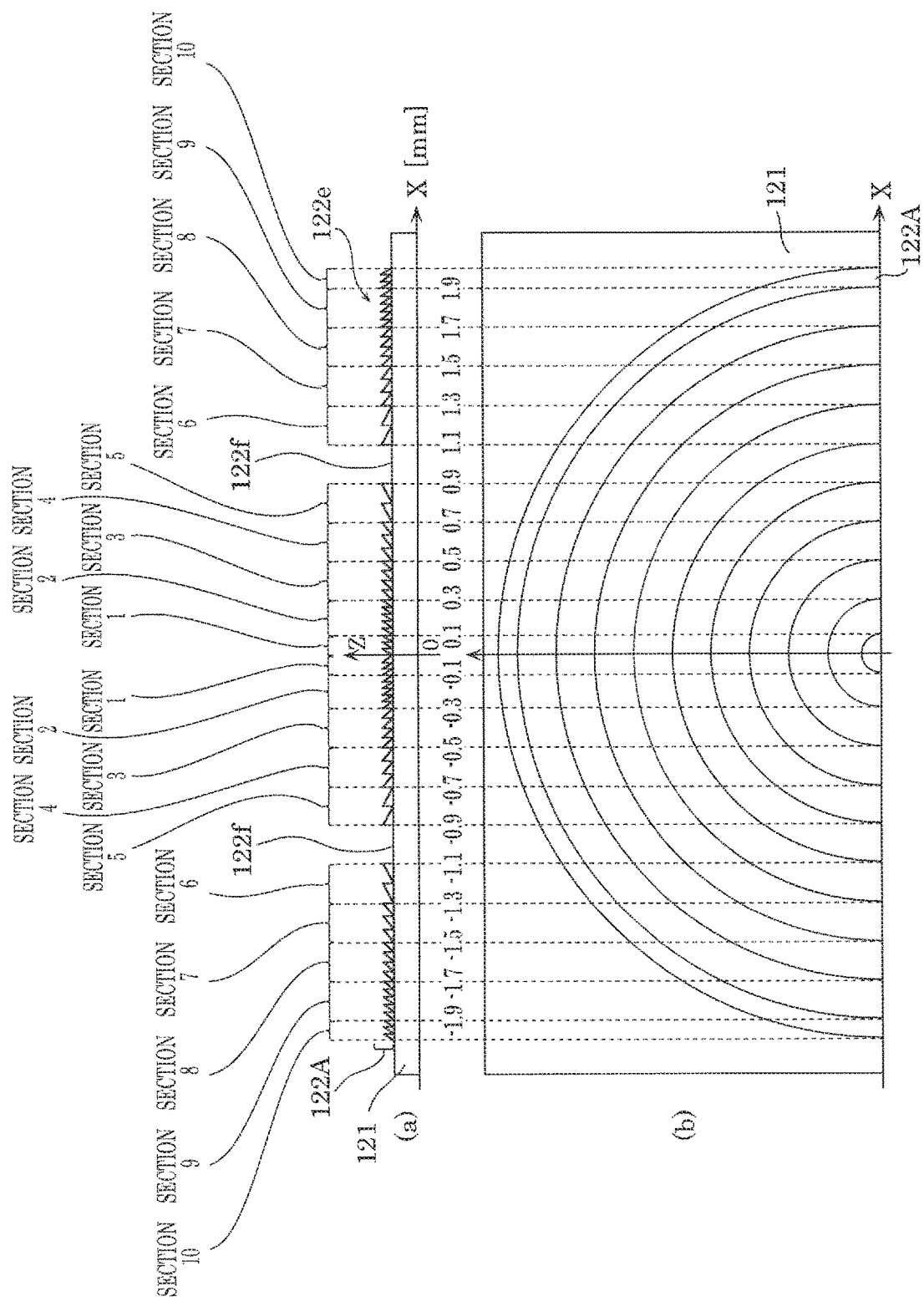

ILLUMINATION LIGHT GUIDING DEVICE AND ENDOSCOPE DEVICE

CROSS REFERENCE TO RELATED APPLICATION

This application claims the benefit of priority of Japanese Patent Application Number 2017-086289 filed on Apr. 25, 2017, the entire content of which is hereby incorporated by reference.

BACKGROUND

1. Technical Field

The present disclosure relates to an illumination light guiding device and an endoscope device with the same.

2. Description of the Related Art

There is an endoscope device that enables a user to view video of an observation target in the body of a subject on a monitor or the like disposed outside the body by inserting a distal end portion of the endoscope device into the body of the subject (for example, Japanese Unexamined Patent Application Publication No. S60-69616).

Japanese Unexamined Patent Application Publication No. S60-69616 discloses a configuration of the distal end portion including an objective lens for forming an image of light from an observation target, an imaging element and lighting means for irradiating the observation target with light. According to a technique disclosed in PTL 1, the lighting means such as a bundle of optical fibers or solid-state light emitting elements is disposed coaxially around the objective lens, whereby it is possible to reduce a space required for the lighting means inside the distal end portion.

SUMMARY

However, in the case where the lighting units includes plural solid-state light emitting elements, the foregoing prior art has a problem that uneven irradiation occurs when the intensity of emitted light is not the same among the plural solid-state light emitting elements. Furthermore, in the case where the lighting means includes a bundle of optical fibers, the foregoing prior art has a problem that uneven irradiation occurs when the bundle of optical fibers is divided into parts, and the intensities of light emitted from respective light sources arranged for the respective parts of the divided bundle are dispersed.

The present disclosure has been made in view of the foregoing problems, and has an object to provide an illumination light guiding device capable of reducing occurrence of uneven irradiation of light to an observation target when the illumination light guiding device is used for an endoscope device, and an endoscope device with the same.

In order to achieve the foregoing object, an illumination light guiding device according to an aspect of the present disclosure includes an optical member that splits an incident laser beam having a predetermined wavelength into laser beams, a lens that substantially collimates the laser beams split by the optical member, a board that is light-transmissive and has one surface onto which the light beams substantially collimated by the lens is incident, a phosphor layer that is disposed on another surface opposite to the one surface of the board, and converts the wavelengths of the light beams that are transmitted through the board and incident on one surface of the phosphor layer, and an emission-side fiber including a plurality of optical fibers that are provided so as to be erected side by side on another surface opposite to the one surface of the phosphor layer, each of the plurality of optical fibers guiding a different one of the light beams having the wavelengths converted by the phosphor layer.

In order to achieve the foregoing object, an endoscope device according to an aspect of the present disclosure includes an insertion portion that is insertable into a body cavity of a subject, and the illumination light guiding device of the foregoing aspect, wherein a distal end portion of the insertion portion includes an objective lens system that forms an image of light from an observation target in the body cavity of the subject, and at least a part of the emission-side fiber, and one end side of the emission-side fiber is coaxially disposed around the objective lens system to illuminate the observation target with each guided light.

An illumination light guiding device according to an aspect of the present disclosure can reduce occurrence of uneven irradiation of light to an observation target when the illumination light guiding device is used for an endoscope device.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 9 is a cross-sectional view and a partial top view of the optical member shown in FIG. 8A.

DETAILED DESCRIPTION OF THE EMBODIMENTS

Embodiments of the present disclosure will be described hereunder. All the embodiments described below are specific examples of the present disclosure. Therefore, numerical values, shapes, materials, constituent elements and the arrangement positions, connection styles, etc. of the constituent elements shown in the following embodiments are examples, and are not subject matters which limit the present disclosure. Therefore, constituent elements which are not recited in independent claims representing the most generic concepts of the present disclosure out of the constituent elements of the following embodiments will be described as optional constituent elements.

Each of the drawings is a schematic diagram, and is not necessarily precisely illustrated. Therefore, scales, etc. in the respective drawings are not necessarily coincident with one another. In the respective drawings, substantially identical constituent elements are assigned the same reference signs, and overlapping descriptions thereof are omitted or simplified.

Embodiment 1

[Endoscope Device]

Figure 1:
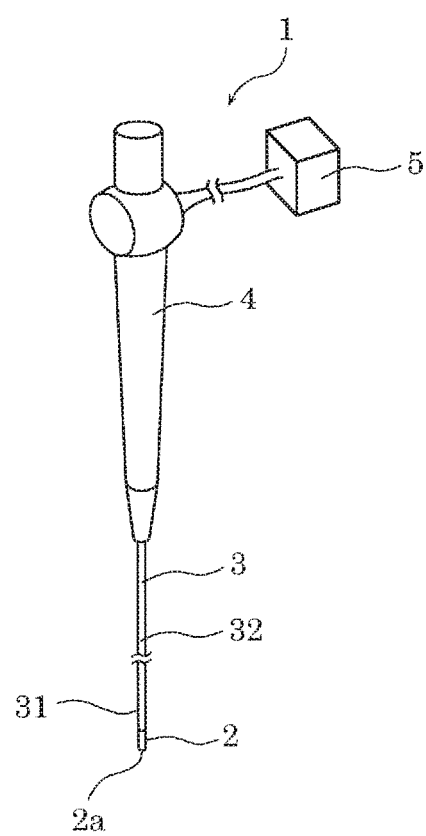
FIG. 1 is a perspective view of an external appearance of an endoscope device with an illumination light guiding device according to Embodiment 1.
Figure 2A:
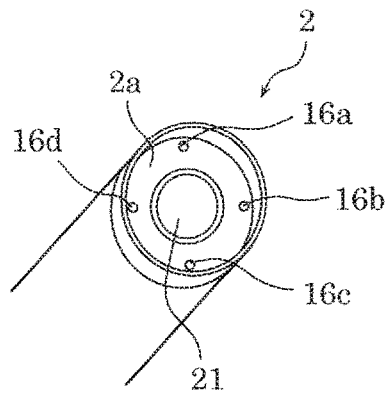
FIG. 2A is a perspective view of an external appearance of a tip face of a distal end portion of the illumination light guiding device according to Embodiment 1.
Figure 2B:
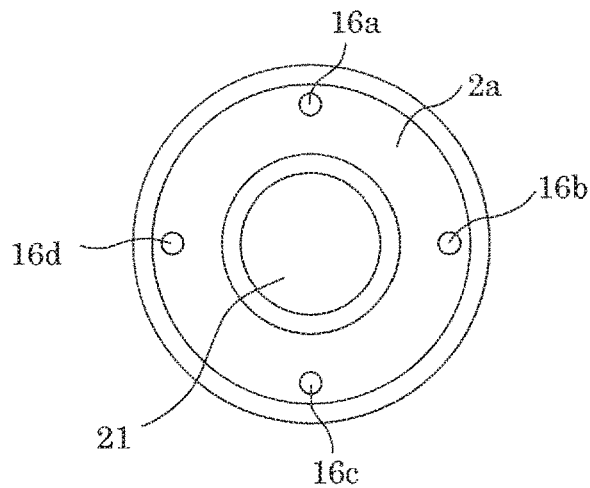
FIG. 2B is a plan view of the distal end portion illustrated in FIG. 2A when the distal end portion is viewed from the tip face side.

An endoscope device will be first exemplified hereunder as an applied product to which an illumination light guiding device according to this embodiment is provided, and an overall configuration thereof will be described with reference to FIG. 1 to FIG. 2B. FIG. 1 is a perspective view of an external appearance of endoscope device 1 with illumination light guiding device 10 according to this embodiment. FIG. 2A is a perspective view of an external appearance of tip face 2a of distal end portion 2 of illumination light guiding device 10 according to Embodiment 1. FIG. 2B is a plan view of distal end portion 2 illustrated in FIG. 2A when distal end portion 2 is viewed from the tip face 2a side.

As illustrated in FIG. 1, endoscope device 1 includes distal end portion 2, insertion portion 3, operation portion 4, and light source device 5. Endoscope device 1 is used, for example, for a surgery, an examination, etc. in a medical field. Video or an image of an observation target in a body can be viewed on a monitor disposed outside the body of a subject by inserting distal end portion 2 and a part of insertion portion 3 into the body of the subject.

<Distal End Portion 2>

Distal end portion 2 constitutes a part of insertion portion 3, that is, a tip portion of insertion portion 3, and distal end portion 2 is hard. Distal end portion 2 has objective lens system 21 for forming an image of light from an observation target. Distal end portion 2 may be configured to include illumination light guiding device 10. The details of illumination light guiding device 10 will be described later.

As shown in FIG. 2A and FIG. 2B, one end side of emission-side fiber 16 including plural optical fibers is coaxially disposed around objective lens system 21 on tip face 2a of distal end portion 2a. The plural optical fibers illuminate the observation target with plural light beams guided therethrough.

In FIG. 2A and FIG. 2B, one end sides of four optical fibers 16a to 16d are coaxially arranged as the one end side of emission-side fiber 16. However, the number of the optical fibers is not limited to four, but it may be set to two or more.

<Insertion Portion 3>

Insertion portion 3 includes, for example, an insertion tube, and is insertable in a body cavity of a subject. Insertion portion 3 includes distal end portion 2, bendable portion 31 linked to distal end portion 2, and flexible portion 32 linked to bendable portion 31. Distal end portion 2, bendable portion 31 and flexible portion 32 are joined to each other in a line. Bendable portion 31 is deformed to be bent in a predetermined direction by operating an operation lever (not illustrated) of operation portion 4. Flexible portion 32 has flexibility with which upon application of external force greater than or equal to a certain level, flexible portion 32 sags and restores while following the external force.

Here, when illumination light guiding device 10 is included in distal end portion 2, an incidence-side fiber including one optical fiber for guiding a laser beam having a predetermined wavelength to illumination light guiding device 10 included in distal end portion 2 is accommodated in insertion portion 3. On the other hand, when illumination light guiding device 10 is included in light source device 5 to be described later, an emission-side fiber as a part of illumination light guiding device 10, that is, the emission-side fiber including plural optical fibers for guiding light to be illuminated to an observation target from tip face 2a of distal end portion 2 is accommodated in insertion portion 3. The incidence-side fiber and the emission-side fiber will be described later.

Furthermore, an image fiber (not illustrated) including a bundle of optical fibers for transmitting an image of the observation target from objective lens system 21, and an operating mechanism (not illustrated) such as an operating wire for bending bendable portion 31 by operating operation portion 4, etc. are accommodated in insertion portion 3.

<Operation Portion 4>

Operation portion 4 is capable of bending bendable portion 31, feeding or sucking air or water from distal end portion 2, and protruding or retracting a treatment tool with the operating mechanism by operating the operation lever.

<Light Source Device 5>

Light source device 5 has a light source for emitting a laser beam having a predetermined wavelength in the wavelength band from ultraviolet light to visible light. Furthermore, light source device 5 may further include illumination light guiding device 10. The light source may be provided not to light source device 5, but to operation portion 4 or distal end portion 2.

In this embodiment, the light source will be described, for example, as a laser light source for emitting a blue laser beam.

[Illumination Light Guiding Device 10]

Figure 3:
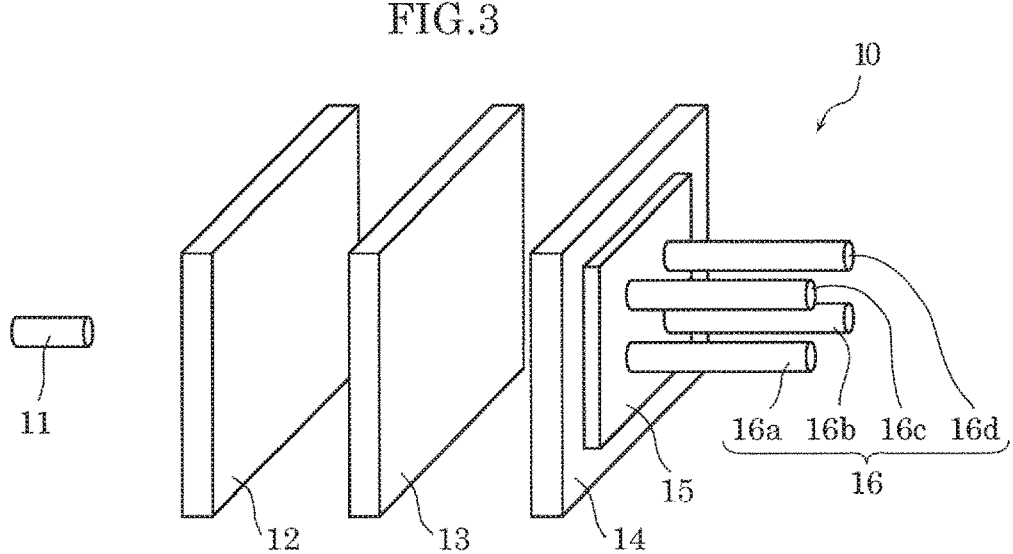
FIG. 3 is a diagram showing an example of a configuration of the illumination light guiding device according to Embodiment 1.

Next, illumination light guiding device 10 according to this embodiment will be described. FIG. 3 is a diagram illustrating an example of a configuration of illumination light guiding device 10 according to Embodiment 1. As shown in FIG. 3, illumination light guiding device 10 includes incidence-side fiber 11, optical member 12, lens 13, board 14, phosphor layer 15 and emission-side fiber 16. Illumination light guiding device 10 may not include incidence-side fiber 11. In this case, incidence-side fiber 11 is not provided at the position of incidence-side fiber 11 shown in FIG. 3.

<Incidence-Side Fiber 11>

Incidence-side fiber 11 includes one optical fiber for guiding a laser beam having a predetermined wavelength. Incidence-side fiber 11 is a transmission path for transmitting a laser beam having a predetermined wavelength emitted from the light source to a remote place. Incidence-side fiber 11 is configured to have a dual structure in which a core having a high refractive index is wrapped by a cladding layer having a lower refractive index than the core. Both the core and the cladding layer are formed of quartz glass or plastic which has remarkably high light transmissivity.

When illumination light guiding device 10 does not include incidence-side fiber 11, a laser light source may be disposed at the position of incidence-side fiber 11 illustrated in FIG. 3 so that a blue laser beam is made directly incident from the disposed laser light source to optical member 12. In short, the disposed laser light source may emit a blue laser beam to optical member 12 by a spatial coupling method. The laser light source and optical member 12 may be in close contact with each other from the viewpoint of reducing the size of illumination light guiding device 10, or may be arranged to be apart from each other by a certain distance from a thermal point of view.

<Optical Member 12>

Figure 4A:
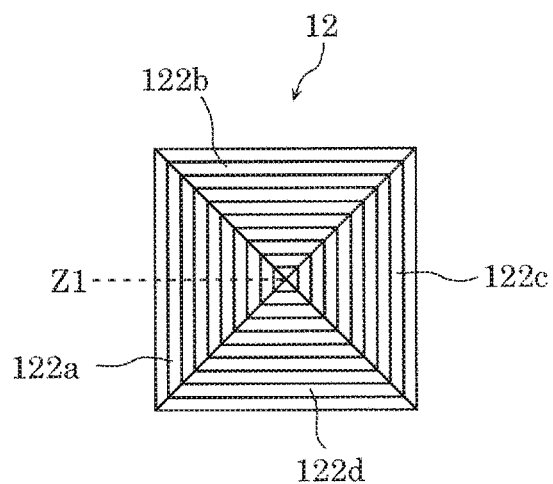
FIG. 4A is a top view of an optical member shown in FIG. 3.
Figure 4B:
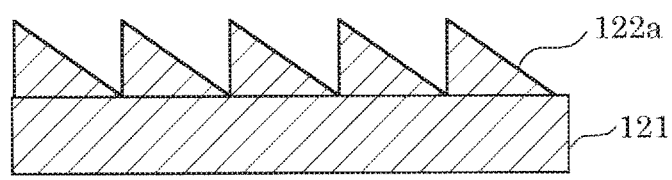
FIG. 4B is a partial cross-sectional view of the optical member shown in FIG. 4A.

FIG. 4A is a top view of optical member 12 illustrated in FIG. 3. FIG. 4B is a partial cross-sectional view of optical member 12 illustrated in FIG. 4A.

Optical member 12 is disposed between incidence-side fiber 11 and lens 13. Optical member 12 may be in contact with or in no contact with incidence-side fiber 11 and lens 13. Optical member 12 splits an incident laser beam. Optical member 12 makes the split light beams incident to lens 13. More specifically, optical member 12 is a light-transmissive diffraction grating, and splits an incident laser beam into plural light beams.

In this embodiment, for example, optical member 12 includes a microlens array that splits and separates a laser beam guided from incidence-side fiber 11 or a laser beam incident directly from the laser light source into plural light beams. This microlens array has plural areas where the arrangement direction of shapes on a plane perpendicular to an incidence face for a laser beam is identical in the same area, but different among different areas.

In the example illustrated in FIG. 3, optical member 12 splits a laser beam guided from incidence-side fiber 11 into four light beams. Optical member 12 is a light-transmissive diffraction grating having a reference face parallel to the incidence face of board 14, and disposed so that the structural center thereof is located on the optical axis of one laser beam guided from incidence-side fiber 11. For example, optical member 12 includes a light-diffractive microlens array, and includes, for example, base material 121 and light-diffractive lens array 122 as illustrated in FIG. 4A and FIG. 4B.

Base material 121 is the base material of the microlens array. Lens array 122 is formed on base material 121. For example, any material such as glass or plastic may be used as a material for forming base material 121. Here, for example, soda glass, non-alkali glass or the like may be used as the glass. Furthermore, for example, acrylic resin, polycarbonate, polyethylene terephthalate (PET), polyethylenenaphthalate (PEN) or the like may be used as the plastic. The material of base material 121 is required to be selected in consideration of heat resistance. Furthermore, it is preferable that base material 121 does not absorb light, and is transparent, and also it is preferable that base material 121 is formed of a material having an extinction coefficient of substantially zero.

Lens array 122 splits and separates a laser beam guided from incidence-side fiber 11 into plural light beams. The cross-sectional shape of lens arrays 122 on the plane perpendicular to the incidence face of lens 13 is serrated, for example. Furthermore, lens array 122 has plural areas where the same arrangement direction of saw teeth is identical in the same area, but different among different areas.

For example, in the example shown in FIG. 4A, lens array 122 has four areas (areas 122a, 122b, 122c, 122d) which are different in the arrangement direction from one another. In the same area of each of the four areas (areas 122a, 122b, 122c, 122d), plural linearly arranged lens arrays are provided, and the arrangement directions of the plural lens arrays are identical to one another. Here, when the wavelength of a laser beam guided from incidence-side fiber 11 is equal to, for example, 460 nm, the grating pitch of the plural lens arrays is equal to, for example, 5 μm, and the grating height is equal to 1 μm.

The cross-sectional shape of lens array 122 on Z1 plane of FIG. 4A is serrated as shown in FIG. 4B. The Z1 plane corresponds to the plane perpendicular to the incidence face of lens 13. The cross-sectional shape of lens array 122 in area 122a is illustrated in FIG. 4B. The cross-sectional shapes of area 122b, area 122c and area 122d are likewise serrated. In other words, lens array 122 corresponds to what is called a blazed diffraction grating. As a result, lens array 122 can enhance the primary diffraction efficiency, and reduce loss (optical loss) of a laser beam guided from incidence-side fiber 11.

For example, as illustrated in top view of FIG. 4A, in lens array 122, the arrangement directions of the saw teeth in the four areas (areas 122a, 122b, 122c, 122d) are different from one another. Such a configuration enables lens array 122 to prevent energy concentration on the incidence face of phosphor layer 15 when lens array 122 splits and separates a laser beam guided from incidence-side fiber 11 to cause the split and separated light beams to enter the incidence face of phosphor layer 15 via lens 13.

The material of lens array 122 is selected according to a forming method, heat resistance and a refractive index of lens array 122. Nanoimprinting, printing, photolithography, EB lithography, particle orientation or the like is available as the method of forming lens array 122. When lens array 122 is formed, for example by nanoimprinting or printing, UV curing resin such as epoxy resin or acrylic resin, or thermoplastic resin such as polymethyl methacrylate (PMMA) may be selected as the material of lens array 122. Furthermore, in consideration of heat resistance, glass or quartz may be selected as the material of lens array 122, and lens array 122 may be formed by photolithography or EB lithography. It is preferable that lens array 122 is formed of a material having the same level refractive index as that of base material 121 so that light from base material 121 easily enters lens array 122. Furthermore, it is preferable that lens array 122 does not absorb light and is transparent as in the case of base material 121, and also it is preferable that lens array 122 is formed of a material whose extinction coefficient is substantially equal to zero.

<Lens 13>

Lens 13 is, for example, a collimator lens, and substantially collimates light beams split by optical member 12. The light beams substantially collimated by lens 13 are incident to board 14.

In this embodiment, lens 13 substantially collimates plural light beams, that is, four light beams split by optical member 12 to cause the four light beams to enter board 14.

<Board 14>

Board 14 that is light-transmissive and includes light beams which are substantially collimated by lens 13 are incident on one surface of board 14. Plural light beams transmitted through board 14 are incident to phosphor layer 15.

In this embodiment, board 14 transmits therethrough the plural light beams, that is, the four incident light beams which are substantially collimated by lens 13 to cause the light beams incident to phosphor layer 15. Any material such as sapphire, ZnO single crystal, AlN, $Y_2O_3$, SiC, polycrystal alumina or GaN may be used as the material for forming board 14 insofar as the material has translucency and a higher thermal conductivity than those of phosphor layer 15. Furthermore, in order to enhance heat dissipation performance more greatly, for example, a heat sink may be attached to board 14 in contact with board 14, or phosphor layer 15 may be sandwiched by two boards 14.

When phosphor layer 15 can be formed without being supported by board 14, illumination light guiding device 10 may include board 14.

<Phosphor Layer 15>

Phosphor layer 15 is disposed on another surface opposite to the one surface of board 14, and converts the wavelengths of light beams which are transmitted through board 14 and incident on the one surface of phosphor layer 15. Phosphor layer 15 converts the wavelength of a part of each of the incident light beams to a light beam in a wavelength band different from the wavelength band of the incident light beam, thereby converting the wavelength of each of the light beams to a light beam having a color different from the color of the former light beam. More specifically, phosphor layer 15 has a function of converting the wavelength of a part of a light beam incident from the one surface (incidence face) which is a left surface illustrated in FIG. 3, and converting the wavelengths of plural light beams incident on the one surface of phosphor layer 15.

In this embodiment, plural blue light beams are transmitted through board 14, and incident to phosphor layer 15, and phosphor layer 15 emits yellow light excited by a part of each of the plural incident blue light beams. Furthermore, phosphor layer 15 emits (transmits) the other part of each of the plural incident blue light beams. In phosphor layer 15, the colors of these blue light beams and yellow light beams are mixed with each other, and emitted from phosphor layer 15, so that phosphor layer 15 emits white light.

Phosphor layer 15 is formed, for example, in a flat-plate shape on board 14 as illustrated in FIG. 3. Phosphor layer 15 contains a phosphor, and is formed by coating the phosphor with a resin such as a silicon resin, an epoxy resin, or the like. When phosphor layer 15 can be formed without being supported by board 14, phosphor layer 15 may be formed alone.

A loss caused by wavelength conversion in phosphor layer 15 changes to heat. Phosphor layer 15 has a temperature quenching characteristic in which the wavelength conversion efficiency decreases when the temperature of phosphor layer 15 increases. Therefore, heat dissipation of phosphor layer 15 is very important. Although not particularly illustrated, the heat dissipation performance may be enhanced by mixing a resin for forming phosphor layer 15 with a material having a high thermal conductivity, for example, an inorganic oxide such as ZnO. The incidence face of phosphor layer 15 may be provided with a microstructure so that light easily enter phosphor layer 15 or heat easily dissipates from the incident face.

<Emission-Side Fiber 16>

Emission-side fiber 16 includes plural optical fibers which are provided to be erected side by side on another surface opposite to the one surface of phosphor layer 15, each of the plural optical fibers guiding a different one of the light beams having the wavelengths converted by phosphor layer 15. More specifically, each of the plural optical fibers of emission-side fiber 16 is a transmission path for guiding a different one of the plural light beams having the wavelengths converted by phosphor layer 15.

In this embodiment, the plural optical fibers constituting emission-side fiber 16 are four optical fibers 16a to 16d. Optical fibers 16a to 16d are provided so as to be erected side by side. Optical fibers 16a to 16d may be provided so as to be erected in parallel to one another. One end of each of optical fibers 16a to 16d is disposed in close contact with or in contact with the position corresponding to the position of each of the plural light beams incident to phosphor layer 15. When illumination light guiding device 10 is used in endoscope device 1, the respective other end sides of four optical fibers 16a to 16d are coaxially arranged around objective lens system 21 at distal end portion 2 of endoscope device 1.

Each of the plural optical fibers constituting emission-side fiber 16 is the same as the optical fiber constituting incidence-side fiber 11. In other words, each of the plural optical fibers is configured to have a dual structure in which a core having a high refractive index is wrapped by a cladding layer having a lower refractive index than the core. Both the core and the cladding layer are formed of quartz glass or plastic which has very high light transmissivity.

[Advantageous Effect, Etc.]

Figure 5:
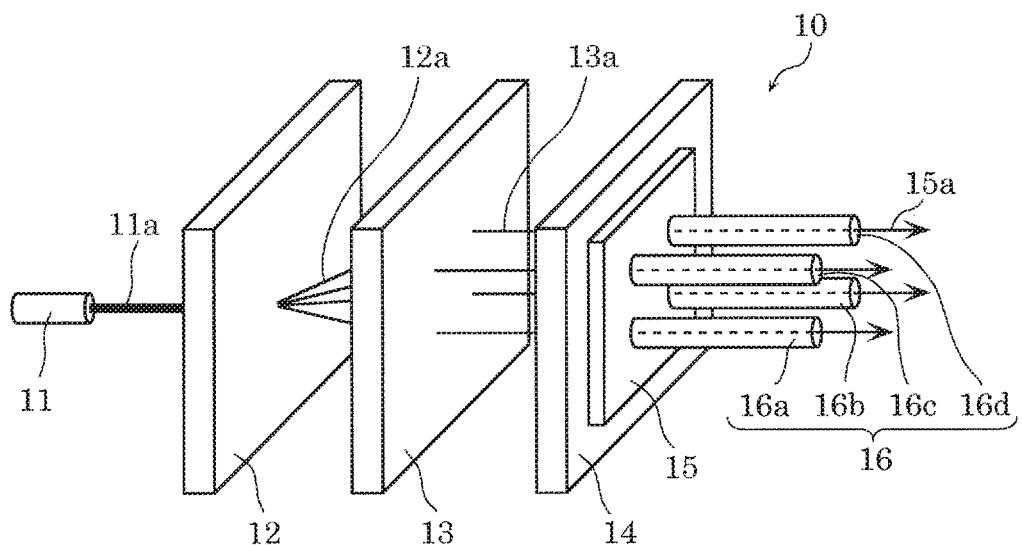
FIG. 5 is a diagram showing an operation of the illumination light guiding device according to Embodiment 1.

FIG. 5 is a diagram illustrating an operation of illumination light guiding device 10 according to this embodiment.

As shown in FIG. 5, in illumination light guiding device 10 according to this embodiment, blue laser beam 11a guided by incidence-side fiber 11 is split and separated into four light beams 12a by optical member 12, and output to the incidence face of lens 13. Four light beams 12a incident to lens 13 are collimated to substantially parallel four light beams 13a by lens 13, and then enter board 14. Light beams 13a incident to board 14 are transmitted through board 14, and then enter phosphor layer 15. In phosphor layer 15, the wavelength of a part of each of four incident light beams 13a is converted to a wavelength in a wavelength band of yellow, thereby converting each of four light beams 13a to white light beam 15a. Four light beams 15a having the wavelengths converted by phosphor layer 15 are incident to one ends of four optical fibers 16a to 16d as emission-side fiber 16 which are provided so as to be erected at corresponding positions. Each of four optical fibers 16a to 16d guides light beam 15a so that guided light beam 15a exits from the other end thereof.

Here, a comparative example will be described.

Figure 6:
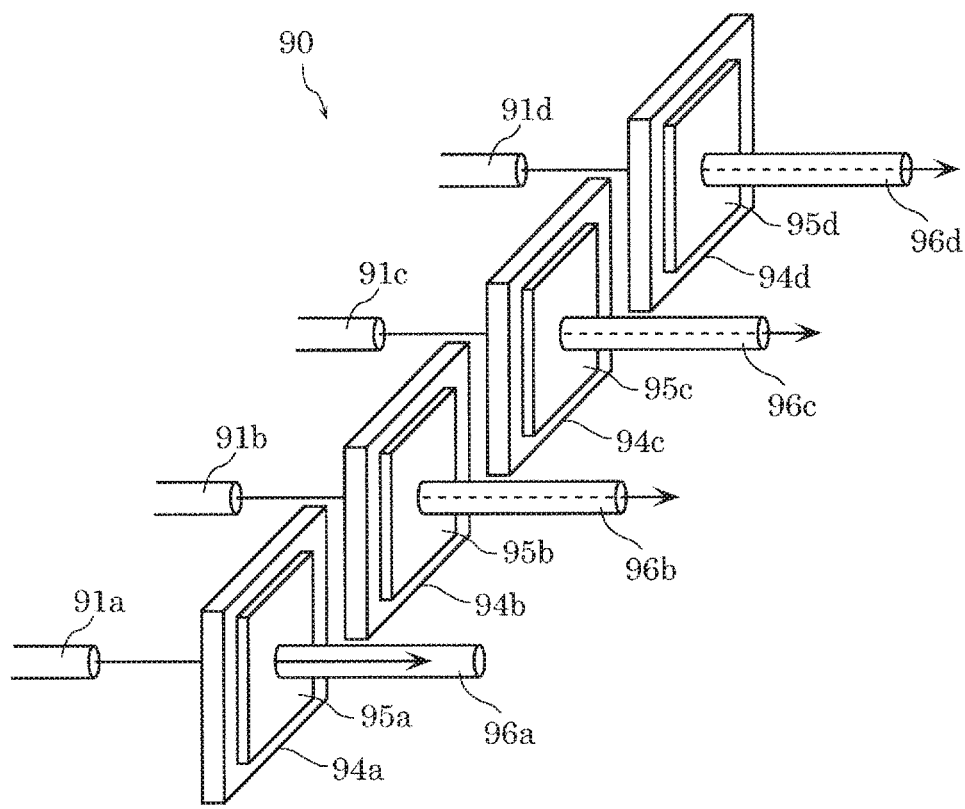
FIG. 6 is a diagram illustrating a configuration of an illumination light guiding device according to a comparative example and an operation thereof.

FIG. 6 is a diagram illustrating a configuration of illumination light guiding device 90 of a comparative example and an operation thereof.

As shown in FIG. 6, illumination light guiding device 90 includes plural incidence-side optical fibers 91a to 91d, plural boards 94a to 94d, plural phosphor layers 95a to 95d, and plural emission-side optical fibers 96a to 96d. In other words, illumination light guiding device 90 of the comparative example does not include optical member for splitting light. Accordingly, a light beam guided by incidence-side optical fiber 91a is transmitted through board 94a, and enters phosphor layer 95a, and then the wavelength of the light beam is converted. The light beam having the converted wavelength enters one end of emission-side optical fiber 96a which is provided to be erected at the position corresponding to the light incidence position on phosphor layer 95a, is guided and then exits from the other end of emission-side optical fiber 96a. The same is applied to light beams to be guided by incidence-side optical fibers 91b to 91d.

As described above, in illumination light guiding device 90 of the comparative example, incidence-side optical fibers 91a to 91d and emission-side optical fibers 96a to 96d are provided in one-to-one correspondence. Therefore, when there is any dispersion among the intensities of light beams which are emitted from light sources and guided by incidence-side optical fibers 91a to 91d, uneven irradiation occurs. Furthermore, when illumination light guiding device 90 including four emission-side optical fibers 96a to 96d is used in distal end portion 2 of endoscope device 1, four incidence-side optical fibers 91a to 91d are required, so that it is impossible to reduce the diameter of insertion portion 3 containing these four incidence-side optical fibers 91a to 91d therein.

On the other hand, in illumination light guiding device 10, by including optical member 12, a laser beam guided through incidence-side fiber 11 configured of one optical fiber can be separated and split (divided) into, for example, four laser beams, and transmitted to four optical fibers 16a to 16d which constitutes emission-side fiber 16 and are arranged side by side. In other words, in illumination light guiding device 10, incidence-side fiber 11 can be configured only of one optical fiber, so that the emitted light intensities of laser beams transmitted to four optical fibers 16a to 16d which constitute emission-side fiber 16 and are arranged side by side are not dispersed, but are equal to one another. Furthermore, when illumination light guiding device 10 is used in distal end portion 2 or light source device 5 of endoscope device 1, a laser beam of one laser source can be separated and split (divided), and then made incident to emission-side fiber 16. Therefore, occurrence of uneven irradiation from an end side (emission side) of emission-side fiber 16 to an observation target can be reduced. Furthermore, since incidence-side fiber 11 of illumination light guiding device 10 can be configured only of one optical fiber, the diameter of insertion portion 3 containing incidence-side fiber 11 therein can be more greatly reduced when illumination light guiding device 10 is used in distal end portion 2 of endoscope device 1.

Furthermore, in illumination light guiding device 10, laser beam 11a guided by incidence-side fiber 11 can be split and separated into four light beams 12a without greatly changing the spot diameter of laser beam 11a to cause four light beams 12a to enter phosphor layer 15. Furthermore, in phosphor layer 15, light beams 13a which have been split and separated and then substantially collimated are incident to different areas on the incidence face, so that energy concentration on the incidence face of phosphor layer 15 can be prevented. In other words, since illumination light guiding device 10 according to this embodiment can further prevent energy concentration on the incidence face of phosphor layer 15, and reduce temperature increase of phosphor layer 15, all the amount of laser beam 11a guided by incidence-side fiber 11 can be output to phosphor layer 15 without any loss. As described above, according to illumination light guiding device 10 according to this embodiment, since the temperature increase in phosphor layer 15 can be reduced even when the energy of laser beam 11a guided by incidence-side fiber 11 is increased, an effect of achieving a high output is also obtained.

As described above, according to illumination light guiding device 10 of this embodiment, when illumination light guiding device 10 of this embodiment is provided in endoscope device 1, occurrence of uneven irradiation of light to an observation target can be reduced. Furthermore, when illumination light guiding device 10 according to this embodiment is provide in distal end portion 2 of endoscope device 1, the diameter of insertion portion 3 can be reduced. Still furthermore, illumination light guiding device 10 according to this embodiment includes optical member 12 for separating and splitting an incident laser beam by diffraction, and thus is capable of increasing the output of laser beam 11a guided by incidence-side fiber 11 while reducing a thermal load on phosphor layer 15.

More specifically, illumination light guiding device 10 according to an aspect of the present disclosure includes optical member 12 that splits an incident laser beam into a plurality of light beams, lens 13 that substantially collimates the plurality of light beams split by optical member 12, board 14 that is light-transmissive and has one surface on which the plurality of light beams substantially collimated by lens 13 are incident, phosphor layer 15 that is disposed on another surface opposite to the one surface of board 14, and converts the wavelengths of the plurality of light beams that are transmitted through board 14 and incident on one surface of phosphor layer 15, and emission-side fiber 16 including a plurality of optical fibers that are provided so as to be erected side by side on another surface opposite to the one surface of phosphor layer 15, each of the plurality of optical fibers guiding a different one of the plurality of light beams having the wavelengths converted by phosphor layer 15.

Accordingly, when illumination light guiding device 10 is used in endoscope device 1, occurrence of uneven irradiation of light to an observation target can be reduced. Here, when illumination light guiding device 10 is used in distal end portion 2 of endoscope device 1, the diameter of insertion portion 3 can be also reduced. Furthermore, temperature increase of phosphor layer 15 can be reduced even when the energy of light to be guided from incidence-side fiber 11 is increased, so that the output of light to be guided by incidence-side fiber 11 can be increased.

Here, for example, optical member 12 is a light-transmissive diffraction grating, and splits an incident laser beam into plural light beams. Phosphor layer 15 converts the wavelengths of plural light beams incident on one surface thereof, and each of plural optical fibers of emission-side fiber 16 guides a different one of the light beams having the wavelengths converted by phosphor layer 15.

As a result, the thickness of optical member 12 can be extremely reduced. When illumination light guiding device 10 is provided in endoscope device 1, the diameter of distal end portion 2 can be reduced more significantly.

Furthermore, for example, optical member 12 includes a microlens array that splits and separates an incident laser beam into plural light beams. The microlens array is a light-transmissive diffraction grating having plural areas where the arrangement direction of shapes on the plane perpendicular to the incidence face for a laser beam is identical in the same area, but different among different areas.

As a result, the energy concentration on the incidence face of phosphor layer 15 can be prevented, so that the output of light to be guided by incidence-side fiber 11 can be increased.

Furthermore, the laser beam is blue light, and phosphor layer 15 may convert the wavelengths of parts of plural incident light beams to light beams of a wavelength band of yellow, so that each of the plural light beams is converted to white light.

In this case, when illumination light guiding device 10 is provided in endoscope device 1, the observation target can be illuminated with white color. As a result, color video of the observation target can be viewed on a monitor.

It is described in this embodiment that optical member 12 is configured of a microlens having four areas where the arrangement direction is different from one another, but the configuration of optical member 12 is not limited to this configuration. Optical member 12 may be a microlens having two or more areas. In this case, the number of the optical fibers constituting emission-side fiber 16 is determined according to the number of these areas. Furthermore, the size of lens array 122 may be larger than the spot diameter of the laser beam guided from incidence-side fiber 11, and any value may be set as the size of lens array 122 on the condition that the light flux of a laser beam guided from incidence-side fiber 11 is not changed.

Embodiment 2

In Embodiment 1, optical member 12 includes the microlens having plural areas whose arrangement directions are different from one another, but optical member 12 is not limited to this configuration. Different points of Embodiment 2 from Embodiment 1 will be mainly described.
[Illumination Light Guiding Device 10A]

Since an applied product to which an illumination light guiding device of this embodiment is provided is the same as described in Embodiment 1, illumination light guiding device 10A according to this embodiment will be described.

Figure 7:
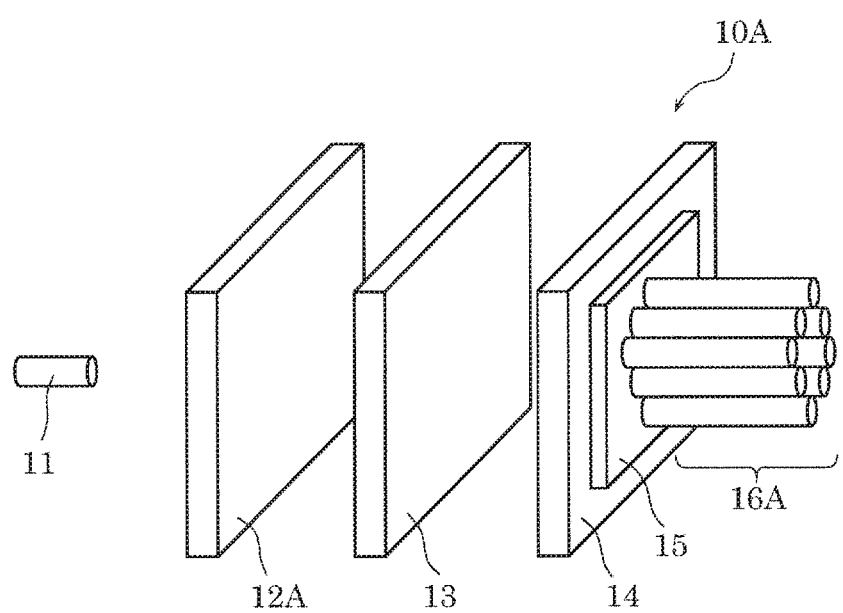
FIG. 7 is a diagram illustrating an example of a configuration of an illumination light guiding device according to Embodiment 2.

FIG. 7 is a diagram showing an example of a configuration of illumination light guiding device 10A according to Embodiment 2. The same elements as those in FIG. 3 are represented by the same reference signs, and detailed descriptions thereof are omitted. Illumination light guiding device 10A shown in FIG. 7 is different from illumination light guiding device 10 according to Embodiment 1 in the configuration of optical member 12A and the configuration of emission-side fiber 16A.
<Optical Member 12A>

Figure 8A:
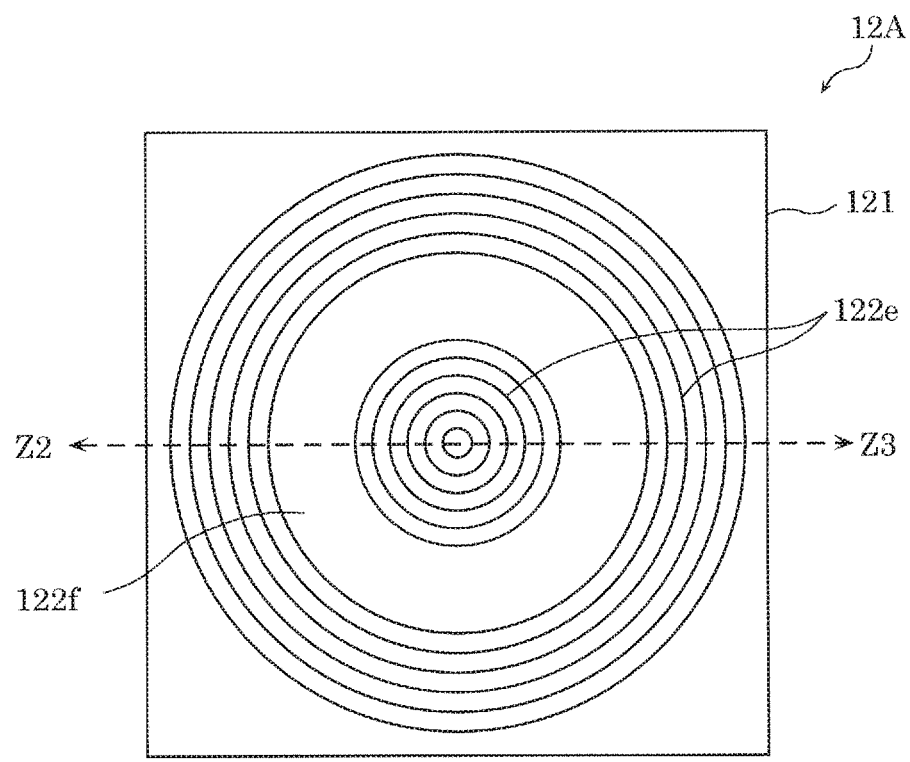
FIG. 8A is a top view of an optical member in Embodiment 2.
Figure 8B:
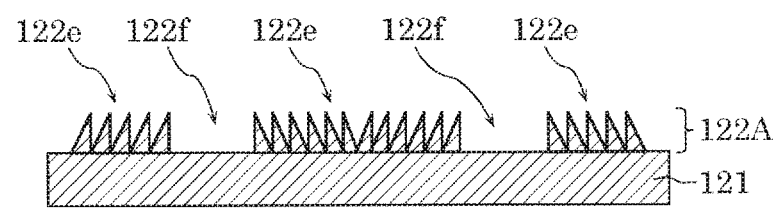
FIG. 8B is a diagram illustrating a cross-sectional view of the optical member shown in FIG. 8A.

FIG. 8A is a top view of optical member 12A in Embodiment 2. FIG. 8B is a diagram showing a cross-sectional view of optical member 12A illustrated in FIG. 8A. FIG. 8B illustrates a cross-sectional view when optical member 12A illustrated in FIG. 8A is cut by a Z2Z3 plane. FIG. 9 is a cross-sectional view and a partial top view of optical member 12A illustrated in FIG. 8A.

Optical member 12A is a diffraction grating disposed between incidence-side fiber 11 and lens 13, and orientates, in a ring shape, a laser beam guided from incidence-side fiber 11 or a laser beam incident directly from a laser light source, thereby splitting the guided laser beam. The light orientated in a ring shape by optical member 12A is caused to enter lens 13.

In this embodiment, optical member 12A orientates the laser beam guided from incidence-side fiber 11 in a ring shape. Here, optical member 12A is a ring-shaped diffraction grating having a reference face parallel to the incidence-face of board 14, and disposed so that the structural center thereof is located on the optical axis of one laser beam guided from incidence-side fiber 11. Optical member 12A is configured, for example, by a diffractive microlens array, and includes base material 121 and lens array 122A as illustrated in FIG. 8A and FIG. 8B, for example.

Base material 121 is the base material of the diffractive microlens array. Specifically, lens array 122A is formed on base material 121. The material for forming base material 121 is the same as described above, and thus description thereof is omitted.

Lens array 122A orientates a laser beam guided from incidence-side fiber 11 in a ring shape, and makes the orientated light incident to lens 13. Lens array 122A is provided on an emission face (on the right side in FIG. 7) of optical member 12A. For example, as illustrated in FIG. 8A and FIG. 8B, lens array 122A includes plural diffraction lenses 122e for diffracting a laser beam guided from incidence-side fiber 11, and straight traveling portion 122f for causing the laser beam guided from incidence-side fiber 11 to travel straight.

A case where lens array 122 has one straight traveling portion 122f will be described below, but lens array 122 may have two or more straight traveling portions. The center of lens array 122A is represented by an intersection point between the X-axis and the Y-axis in an example shown in (b) of FIG. 9, and represented by the Z-axis in an example shown in (a) of FIG. 9. In the example shown in (a) of FIG. 9, the direction from the center of lens array 122A to the periphery thereof is represented by a direction away from the Z-axis along the X-axis. This holds true for a direction away from the Z-axis along the Y-axis, and thus the direction is not illustrated. Descriptions are given assuming that the spot diameter of the laser beam guided from incidence-side fiber 11 is 3 mm, the thickness of base material 121 is 1 mm, and the diameter of lens array 122A is 4 mm.

As illustrated in FIG. 8A, straight traveling portion 122f corresponds to an annular area in which plural diffraction lenses 122e are not provided when optical member 12A is viewed from top side, and is provided to have a flat surface which is substantially parallel to the emission face of optical member 12A. More specifically, as illustrated in FIG. 8B and (a) of FIG. 9, straight traveling portion 122f is provided in an area of the surface of lens array 122A where plural diffraction lenses 122e are not provided, so that the area becomes a flat surface which is substantially parallel to the upper surface of base material 121 (the emission face of optical member 12A). As illustrated in (a) of FIG. 9, straight traveling portion 122f causes light incident from the negative side of the Z-axis to travel straight directly (without diffracting the light, or the like). In the example illustrated in (a) of FIG. 9, since the spot diameter of the laser beam guided from incidence-side fiber 11 is 3 mm, straight traveling portion 122f is provided in an area between a circle having a radius of 0.9 mm and a circle having a radius of 1.1 mm and having the center (Z-axis) of lens array 122A as the origin.

As illustrated in FIG. 8A, plural diffraction lenses 122e are concentrically provided on the emission face of optical member 12A when optical member 12A is viewed from top side. As illustrated in FIG. 8B and (a) of FIG. 9, the cross-sectional shape of plural diffraction lenses 122e on a plane perpendicular to the emission face is serrated. Here, the pitch of plural diffraction lenses 122e differs for each predetermined section.

More specifically, as illustrated in FIG. 8B and (a) of FIG. 9, the plural diffraction lenses are concentrically provided in areas which are not provided with straight traveling portion 122f on the surface portion of lens array 122A so that the pitch of plural diffraction lenses differs for each predetermined section. Since the cross-sectional shapes of plural diffraction lenses 122e on a plane perpendicular to the emission face are serrated, lens array 122A corresponds to what is called blazed diffraction grating. As a result, lens array 122A can enhance the primary diffraction efficiency, and reduce a loss (optical loss) of the laser beam guided from incidence-side fiber 11.

The pitch of plural diffraction lenses 122e is set to increase as the position thereof shifts from the center of optical member 12A to straight traveling portion 122f and decrease as the position thereof shifts from straight traveling portion 122f to the outside in top view. More specifically, as illustrated in (a) of FIG. 9, the pitch of plural diffraction lenses 122e is set to be identical in the same section, but differ among section 1 to section 5 and among section 6 to section 10. Furthermore, the pitch of the plural diffraction lenses is set to be larger as the position thereof is closer to straight traveling portion 122f in a way that the pitch in section 2 is larger than that in section 1, the pitch in section 3 is larger than that in section 2, etc. In the example shown in FIG. 9, section 1 is a region between a circle having a radius of 0 mm and a circle having a radius of 0.1 mm with the Z-axis set as the origin of the circles, section 2 is a region between a circle having a radius of 0.1 mm and a circle having a radius of 0.3 mm with the Z-axis set as the origin of the circles, section 3 is a region between a circle having a radius of 0.3 mm and a circle having a radius of 0.5 mm with the Z-axis set as the origin of the circles, section 4 is a region between a circle having a radius of 0.5 mm and a circle having a radius of 0.7 mm with the Z-axis set as the origin of the circles, section 5 is a region between a circle having a radius of 0.7 mm and a circle having a radius of 0.9 mm with the Z-axis set as the origin of the circles, and section 6 is a region between a circle having a radius of 1.1 mm and a circle having a radius of 1.3 mm with the Z-axis set as the origin of the circles. Section 7 is a region between a circle having a radius of 1.3 mm and a circle having a radius of 1.5 mm with the Z-axis set as the origin of the circles, and section 8 is a region between a circle having a radius of 1.5 mm and a circle having a radius of 1.7 mm with the Z-axis set as the origin of the circles. Section 9 is a region between a circle having a radius of 1.7 mm and a circle having a radius of 1.9 mm with the Z-axis set as the origin of the circles, and section 10 is a region between a circle having a radius of 1.9 mm and a circle having a radius of 2 mm with the Z-axis set as the origin of the circles. Each of sections 2 to 10 is provided as an annular region having a width of 2 mm.

In the example illustrated in FIG. 9, the grating height of plural diffraction lenses 122e is 0.9 μm. The grating pitches in section 1 and section 10 are 2.3 μm, and the grating pitches in section 2 and section 9 are 2.9 μm. The grating pitches in section 3 and section 8 are μm. The grating pitches in section 5 and section 6 are 11.3 μm. As described above, the pitch of plural diffraction lenses 122e increases as the position thereof shifts from the center of optical member 12A to straight traveling portion 122f, and decreases as the position thereof shifts from straight traveling portion 122f to the outside in top view.

Plural diffraction lenses 122e provided as described above are capable of diffracting a laser beam incident from the negative side of the Z-axis and guided from incidence-side fiber 11 so as to direct the diffracted light to light traveling straight through straight traveling portion 122f.

Thus-configured lens array 122A can orientate the laser beam guided from incidence-side fiber 11 in a ring shape. Accordingly, the light orientated in a ring shape is substantially collimated in lens 13, and incident to phosphor layer 15, so that energy concentration on the incidence face of phosphor layer 15 can be prevented.

The material for lens array 122A is the same as lens array 122, and thus a description thereof is omitted.

<Emission-Side Fiber 16A>

Emission-side fiber 16A includes plural optical fibers which are provided so as to be erected side by side on another surface opposite to one surface of phosphor layer 15, and guide respective light beams having the wavelengths converted by phosphor layer 15. More specifically, each of the plural optical fibers of emission-side fiber 16A is a transmission path for guiding a part of ring-shaped light beams having the wavelengths converted by phosphor layer 15.

That is, emission-side fiber 16A illustrated in FIG. 7 is different from emission-side fiber 16 illustrated in FIG. 3 in the number of optical fibers constituting emission-side fiber 16A. In the example illustrated in FIG. 7, emission-side fiber 16A includes eight optical fibers, but the configuration of emission-side fiber 16A is not limited to this configuration.

The plural optical fibers constituting emission-side fiber 16A are provided so as to be erected side by side. The plural optical fibers constituting emission-side fiber 16A may be provided so as to be erected in parallel to one another. One end of each of the plural optical fibers constituting emission-side fiber 16A is disposed to be in close contact with or in contact with the position corresponding to the position of a part of ring-shaped light incident to phosphor layer 15. When illumination light guiding device 10A is used provided endoscope device 1, the other end sides of the plural optical fibers constituting emission-side fiber 16A are coaxially arranged around objective lens system 21 in distal end portion 2 of endoscope device 1.

Since each of the plural optical fibers constituting emission-side fiber 16A is similar to the optical fibers constituting incidence-side fiber 11 and emission-side fiber 16A, the description thereof is omitted hereunder.

[Advantageous Effect, Etc.]

Figure 10:
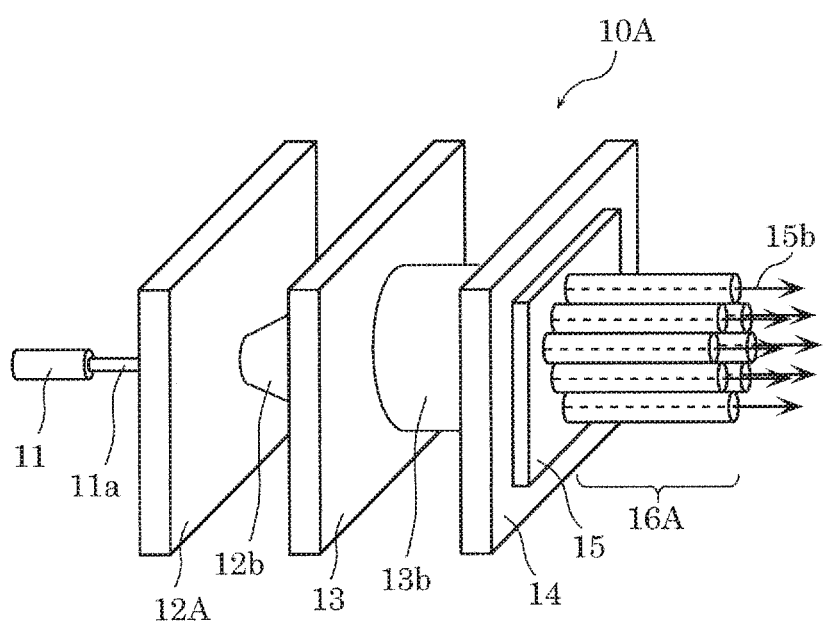
FIG. 10 is a diagram illustrating an operation of the illumination light guiding device according to Embodiment 2.

FIG. 10 is a diagram illustrating an operation of illumination light guiding device 10A according to Embodiment 2.

As illustrated in FIG. 10, in illumination light guiding device 10A according to this embodiment, blue laser beam 11a guided by incidence-side fiber 11 is orientated to ring-shaped light beams 12b in optical member 12A, and emitted to incidence face of lens 13. Ring-shaped light beams 12b incident to lens 13 are collimated to substantially parallel light beams 13b in lens 13, and caused to enter board 14. Light beams 13b incident to board 14 are transmitted through board 14, and caused to enter phosphor layer 15. In phosphor layer 15, the wavelengths of a part of incident ring-shaped light beams 13b are converted to wavelengths in a wavelength band of yellow, thereby converting ring-shaped light 13b to white light. The white light having the wavelength converted by phosphor layer 15 enters one ends of the plural optical fibers as emission-side fiber 16A, each of the plural optical fibers being provided so as to be erected at the position corresponding to a part of the white light. Light 15b incident to one end of each of the plural optical fibers which constitute emission-side fiber 16A is guided and exits from the other end thereof.

As described above, in illumination light guiding device 10A, by including optical member 12A, a laser beam guided through incidence-side fiber 11 configured of one optical fiber can be orientated (divided) in a ring shape, and transmitted to the plural optical fibers which constitute emission-side fiber 16 and are arranged side by side. In other words, since incidence-side fiber 11 can be configured only of the one optical fiber in illumination light guiding device 10A, the emitted light intensities of laser beams transmitted to the plural optical fibers which constitute emission-side fiber 16A and are arranged side by side are identical to one another without dispersion. Furthermore, since incidence-side fiber 11 can be configured only of one optical fiber in illumination light guiding device 10A, when illumination light guiding device 10A is provided in distal end portion 2 of endoscope device 1, the diameter of insertion portion 3 can be reduced, and the light can be orientated (divided) on a side near to the other end side (emission side) of emission-side fiber 16A inside distal end portion 2, so that occurrence of uneven irradiation of light to an observation target body can be further reduced.

As described above, according to illumination light guiding device 10A of this embodiment, when illumination light guiding device 10A is used in endoscope device 1, occurrence of uneven irradiation of light to an observation target can be reduced, and when illumination light guiding device 10A is used in distal end portion 2 of endoscope device 1, the diameter of insertion portion 3 can be reduced. Furthermore, illumination light guiding device 10A according to this embodiment includes optical member 12A for orientating an incident laser beam in a ring shape, and thus is capable of increasing the output of laser beam 11a guided by incidence-side fiber 11 while reducing the thermal load on phosphor layer 15.

More specifically, illumination light guiding device 10A according to an aspect of the present disclosure includes optical member 12A that splits an incident laser beam, lens 13 that substantially collimates light beams split by optical member 12A, board 14 that is light-transmissive and has one surface on which the light substantially-collimated in lens 13 is incident, phosphor layer 15 that is disposed on another surface opposite to the one surface of board 14, and converts the wavelengths of the light beams transmitted through board 14 and incident on one surface thereof, and emission-side fiber 16A including a plurality of optical fibers that are provided so as to be erected side by side on another surface opposite to the one surface of phosphor layer 15, and respectively guide the light beams having the wavelengths converted by phosphor layer 15.

As a result, when illumination light guiding device 10A is provided in endoscope device 1, occurrence of uneven irradiation of light to an observation target can be reduced, and when illumination light guiding device 10A is used in distal end portion 2 of endoscope device 1, the diameter of insertion portion 3 can be reduced. Furthermore, temperature increase in phosphor layer 15 can be reduced even when energy of light to be guided from incidence-side fiber 11 is increased, so that the output of light to be guided by incidence-side fiber 11 can be increased.

Here, for example, optical member 12A is a diffraction grating, and orientates a laser beam guided from incidence-side fiber 11 in a ring shape to split the laser beam. Each of the plural optical fibers of emission-side fiber 16A guides a different part of light beams having the wavelengths converted by phosphor layer 15.

As a result, optical member 12 can be formed so that the thickness thereof is remarkably small. When illumination light guiding device 10A is provided in endoscope device 1, the diameter of distal end portion 2 can be further reduced.

Furthermore, the number of optical fibers constituting emission-side fiber 16A can be increased by orientating a guided laser beam in a ring shape. As a result, an observation target can be illuminated with uniform light even when the motion of distal end portion 2 of endoscope device 1 is large. Therefore, even when the observation target is an object in a bowel in the dark, bright uniform pictures can be captured by endoscope device 1.

Furthermore, by orientating a guided laser beam in a ring shape, thermal load on phosphor layer 15 can be reduced, that is, energy concentration on the incidence face of phosphor layer 15 can be prevented, so that the output of light to be guided by incidence-side fiber 11 can be increased.

Other Embodiments, Etc

The foregoing embodiments are merely examples, and it is needless to say that various alterations, additions, omissions, etc. may be made to the embodiments.

Configurations implemented by arbitrarily combining the constituent elements and functions presented in the foregoing embodiments are included in the scope of the present disclosure. Additionally, the present disclosure covers configurations obtained by adding various modifications to the foregoing embodiments which may be arrived at by a person skilled in the art, and configurations implemented by arbitrarily combining the constituent elements and functions in the respective embodiments without departing from the scope of the present disclosure.

For example, endoscope device 1 with illumination light guiding device 10 (or 10A) in any of the foregoing embodiments is also included in the present disclosure. Specifically, endoscope device 1 according to an aspect of the present disclosure includes insertion portion 3 insertable in a body cavity of a subject, and illumination light guiding device 10 (or 10A). Distal end portion 2 of insertion portion 3 includes objective lens system 21 for forming an image of light from an observation target in the body cavity of the subject, and at least a part of emission-side fiber 16 (or 16A). Emission-side fiber 16 (or 16A) is configured so that end side thereof is coaxially disposed around objective lens system 21 to illuminate the observation target with each guided light.

When illumination light guiding device 10 (or 10A) in any of the foregoing embodiments is used for light source 5 of endoscope device 1, and a part of emission-side fiber 16 (or 16A) of illumination light guiding device 10 (or 10A) is configured in distal end portion 2, occurrence of uneven irradiation of light to the observation target can be reduced. Furthermore, when illumination light guiding device 10 (or 10A) in the foregoing embodiments is provided in distal end portion 2 of endoscope device 1, the diameter of insertion portion 3 can be reduced, and occurrence of uneven irradiation of light to the observation target can be reduced.

Furthermore, illumination light guiding device 10 (or 10A) in the foregoing embodiments may be used for a camera portion of a robot. As in the case where an illumination light guiding device is provided in endoscope device 1, not only the camera portion to which illumination light guiding device 10 (or 10A) is attached can be miniaturized, but also occurrence of uneven irradiation of light to the observation target can be reduced.

What is claimed is:
1. An illumination light guiding device, comprising:
an optical member that splits an incident laser beam having a predetermined wavelength into a plurality of laser beams;
a lens that collimates the plurality of laser beams split by the optical member into collimated light beams;
a board that is light-transmissive and has one surface on which the light beams collimated by the lens are incident;
a phosphor layer that is disposed on another surface opposite to the one surface of the board, and converts wavelengths of the light beams that are transmitted through the board and incident on one surface of the phosphor layer; and
an emission-side fiber including a plurality of optical fibers that are provided so as to be erected side by side on another surface opposite to the one surface of the phosphor layer, each of the plurality of optical fibers guiding a different one of the light beams having wavelengths converted by the phosphor layer.

2. The illumination light guiding device according to claim 1, wherein the optical member is a light-transmissive diffraction grating, and splits the incident laser beam into a plurality of light beams which are the plurality of laser beams, the phosphor layer converts the wavelengths of the plurality of light beams incident on the one surface, and each of the plurality of optical fibers of the emission-side fiber guides a different one of the plurality of light beams having wavelengths converted by the phosphor layer.

3. The illumination light guiding device according to claim 2, wherein the optical member includes a microlens array that splits and separates the incident laser beam into a plurality of light beams, and a face of the microlens array is split into a plurality of different areas each having an arrangement of shapes, with the shapes within a same area being arranged to face in a same direction, and a direction in which the shapes within one area face being different from a direction in which the shapes within a different area face.

4. The illumination light guiding device according to claim 1, wherein the optical member is a diffraction grating, and orientates the incident laser beam in a ring shape to split the laser beam, and each of the plurality of optical fibers of the emission-side fiber guides a part of the light beams having wavelengths converted by the phosphor layer.

5. An endoscope device, comprising:

an insertion portion that is insertable into a body cavity of a subject; and the illumination light guiding device according to claim 1, wherein a distal end portion of the insertion portion includes:

an objective lens system that forms an image of light from an observation target in the body cavity of the subject; and at least a part of the emission-side fiber, and one end side of the emission-side fiber is coaxially disposed around the objective lens system to illuminate the observation target with each guided light beam.

* * * * *